United States Patent
Benedict et al.

(10) Patent No.: US 12,075,999 B2
(45) Date of Patent: Sep. 3, 2024

(54) KNOTLESS TENSIONABLE FIXATION SYSTEMS AND SURGICAL METHODS FOR REPAIRING TISSUE DEFECTS

(71) Applicant: ARTHREX, INC., Naples, FL (US)

(72) Inventors: Robert J. Benedict, Fort Meyers, FL (US); Thomas Dooney, Jr., Naples, FL (US); Alan M. Hirahara, Gold River, CA (US)

(73) Assignee: ARTHREX, INC., Naples, FL (US)

( * ) Notice: Subject to any disclaimer, the term of this patent is extended or adjusted under 35 U.S.C. 154(b) by 315 days.

(21) Appl. No.: 17/522,972

(22) Filed: Nov. 10, 2021

(65) Prior Publication Data
US 2023/0147972 A1    May 11, 2023

(51) Int. Cl.
 A61B 17/04    (2006.01)
 A61F 2/46    (2006.01)
 A61B 17/00    (2006.01)
 A61F 2/30    (2006.01)

(52) U.S. Cl.
 CPC ........ A61B 17/0401 (2013.01); A61F 2/4601 (2013.01); *A61B 2017/00004* (2013.01);
 (Continued)

(58) Field of Classification Search
 CPC .. A61F 2/02; A61F 2/08; A61F 2/0805; A61F 2/0811; A61F 2002/0817; A61F 2002/0876; A61F 2002/0847; A61F 2002/0823; A61F 2002/0841; A61F 2002/0852; A61F 2002/0858; A61F 2002/0864; A61F 2002/087; A61F 2002/0882; A61F 2002/0888; A61F 2/28; A61F 2/2846; A61F 2002/285; A61F 2/30756; A61F 2/40; A61F 2/32; A61F 2/38; A61F 2/42; A61F 2/34; A61F 2/36;
 (Continued)

(56) References Cited

U.S. PATENT DOCUMENTS 7,550,007 B2    6/2009    Malinin
10,524,774 B2    1/2020    Benedict et al.
 (Continued)

FOREIGN PATENT DOCUMENTS

EP    3753497 A1    12/2020

OTHER PUBLICATIONS

International Search Report and Written Opinion of the International Searching Authority for International Application No. PCT/US2022/049206 dated Feb. 23, 2023.
International Preliminary Report on Patentability for International application No. PCT/US2022/049206 dated May 23, 2024.

*Primary Examiner* — Katherine M Shi
(74) *Attorney, Agent, or Firm* — Carlson, Gaskey & Olds, P.C.

(57) ABSTRACT

A knotless tensionable fixation system may be utilized for performing surgical methods for repairing tissue defects within a joint. An exemplary surgical method may include fixating a graft over top of the tissue defect with the knotless tensionable knotless fixation system. The knotless tensionable fixation system may include a plurality of knotless suture anchors, the graft, and a reinforcement construct. The reinforcement construct may establish a fixed segment of material over the graft after being secured in place by the plurality of knotless suture anchors.

20 Claims, 9 Drawing Sheets

(52) U.S. Cl.
CPC .......... *A61B 2017/0414* (2013.01); *A61F 2002/30461* (2013.01)

(58) Field of Classification Search
CPC ....... A61F 2002/30461; A61B 17/0401; A61B 17/0483; A61B 2017/0404; A61B 2017/0406; A61B 2017/0414; A61B 2017/564; A61B 2017/00004; A61B 2017/0409; A61B 2017/044; A61B 2017/0464; A61B 17/0469; A61B 17/06166; A61B 2017/06185
See application file for complete search history.

(56) References Cited

U.S. PATENT DOCUMENTS

| | | |
|---|---|---|
| 10,792,403 B2 | 10/2020 | Benedict et al. |
| 2007/0191849 A1 | 8/2007 | ElAttrache et al. |
| 2007/0288023 A1* | 12/2007 | Pellegrino .......... A61B 17/0401 606/232 |
| 2008/0262616 A1* | 10/2008 | McKay ................ A61F 2/28 623/14.12 |
| 2008/0275431 A1* | 11/2008 | Stone ................ A61B 17/0401 606/1 |
| 2012/0265219 A1* | 10/2012 | Rushdy .............. A61B 17/0401 606/139 |
| 2015/0032157 A1 | 1/2015 | Dooney, Jr. et al. |
| 2017/0360425 A1 | 12/2017 | Stone et al. |
| 2018/0049734 A1* | 2/2018 | Kam ................ A61B 17/06166 |
| 2020/0253715 A1* | 8/2020 | Trenhaile .............. A61F 2/0811 |
| 2021/0154001 A1 | 5/2021 | Adams et al. |

\* cited by examiner

KNOTLESS TENSIONABLE FIXATION SYSTEMS AND SURGICAL METHODS FOR REPAIRING TISSUE DEFECTS

BACKGROUND

This disclosure relates to the field of surgery, and more particularly to knotless tensionable fixation systems and associated surgical methods for repairing tissue defects.

Repetitive trauma to a joint, such as a knee, ankle, hip, or shoulder joint, for example, may result in the development of tissue defects (e.g., cartilage defects, soft tissue tears, etc.). If not treated, tissue defects could further deteriorate, thereby causing joint instability and discomfort.

SUMMARY

This disclosure relates to knotless tensionable fixation systems and surgical methods for repairing tissue defects within a vessel or canal of a joint.

An exemplary surgical method for repairing a tissue defect may include, inter alia, inserting a first knotless suture anchor into a bone, creating a first loop in the first knotless suture anchor, inserting a second knotless suture anchor into the bone, creating a second loop in the second knotless suture anchor, passing the first loop and the second loop through a graft, passing a reinforcement construct through the first loop or looping the reinforcement construct about the first loop, passing the reinforcement construct through the second loop or looping the reinforcement construct about the second loop, tightening the first loop down to the graft to approximate the graft to the tissue defect, tightening the second loop down to the graft to further approximate the graft to the tissue defect, securing a first tail portion of the reinforcement construct to the bone with a third knotless suture anchor, and securing a second tail portion of the reinforcement construct to the bone with a fourth knotless suture anchor. The reinforcement construct extends over top of the graft to compresses the graft to the tissue defect after securing the first and second tail portions.

Another exemplary surgical method may include, inter alia, fixating a graft over top of a tissue defect with a knotless tensionable knotless fixation system. The knotless tensionable fixation system includes a plurality of knotless suture anchors, the graft, and a reinforcement construct. The reinforcement construct establishes a fixed segment of material over the graft and is secured in place by the plurality of knotless suture anchors.

An exemplary knotless tensionable fixation system for repairing a tissue defect may include, inter alia, a plurality of knotless suture anchors, an osteochondral allograft, and a reinforcement construct that is connectable to the plurality of knotless suture anchors and configured for fixating the osteochondral allograft over top of the tissue defect.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
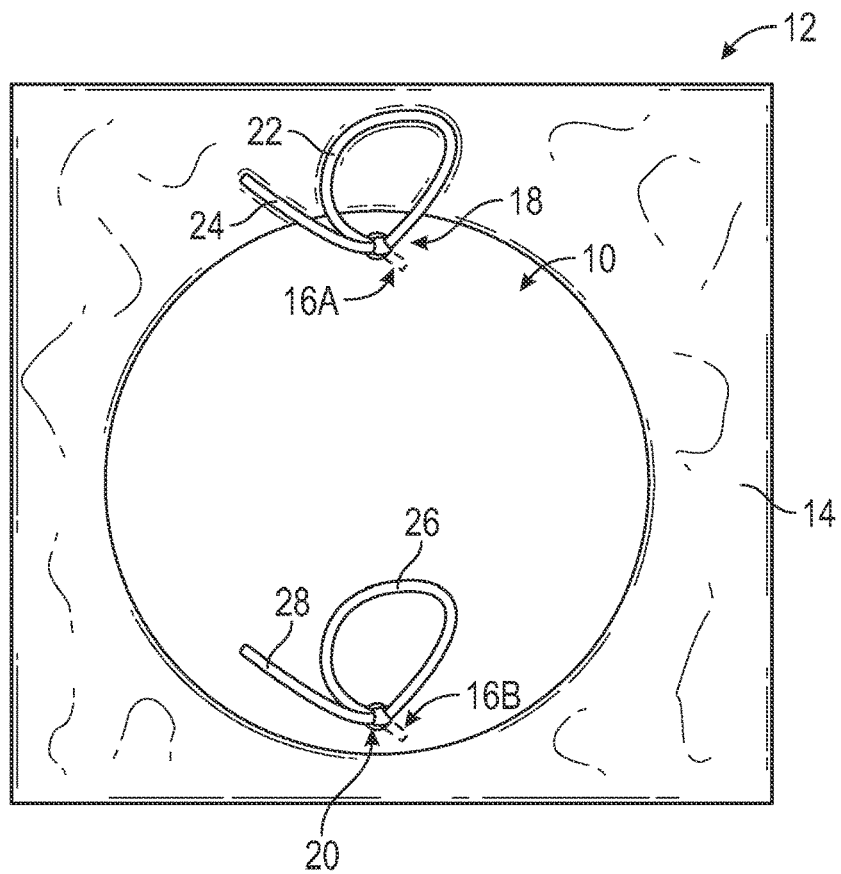
FIG. 1 schematically illustrates a step of surgical method for repairing a tissue defect using a knotless tensionable fixation system.

This disclosure is directed to knotless tensionable fixation systems and surgical methods for repairing tissue defects within a joint. The system and methods described herein may be utilized to secure a graft over the tissue defect for providing a tissue network that can potentially signal autologous cellular interactions. These and other features of this disclosure are described in further detail below.

An exemplary surgical method for repairing a tissue defect may include, inter alia, inserting a first knotless suture anchor into a bone, creating a first loop in the first knotless suture anchor, inserting a second knotless suture anchor into the bone, creating a second loop in the second knotless suture anchor, passing the first loop and the second loop through a graft, passing a reinforcement construct through the first loop or looping the reinforcement construct about the first loop, passing the reinforcement construct through the second loop or looping the reinforcement construct about the second loop, tightening the first loop down to the graft to approximate the graft to the tissue defect, tightening the second loop down to the graft to further approximate the graft to the tissue defect, securing a first tail portion of the reinforcement construct to the bone with a third knotless suture anchor, and securing a second tail portion of the reinforcement construct to the bone with a fourth knotless suture anchor. The reinforcement construct extends over top of the graft to compresses the graft to the tissue defect after securing the first and second tail portions.

In a further embodiment, a graft configured for repairing a tissue defect is an osteochondral allograft.

In a further embodiment, a graft configured for repairing a tissue defect is a dermal allograft.

In a further embodiment, a reinforcement construct of a knotless tensionable fixation system is an absorbable suture.

In a further embodiment, a reinforcement construct of a knotless tensionable fixation system is a nonabsorbable suture.

Another exemplary surgical method may include, inter alia, fixating a graft over top of a tissue defect with a knotless tensionable knotless fixation system. The knotless tensionable fixation system includes a plurality of knotless suture anchors, the graft, and a reinforcement construct. The reinforcement construct establishes a fixed segment of material over the graft and is secured in place by the plurality of knotless suture anchors.

In a further embodiment, fixating a graft over top of a tissue defect with a knotless tensionable knotless fixation system includes inserting a first knotless suture anchor into a bone, creating a first loop in the first knotless suture anchor, inserting a second knotless suture anchor into the bone, and creating a second loop in the second knotless suture anchor.

In a further embodiment, fixating a graft over top of a tissue defect with a knotless tensionable knotless fixation system includes passing a first loop and a second loop through a graft.

In a further embodiment, fixating a graft over top of a tissue defect with a knotless tensionable fixation system includes connecting a reinforcement construct to a first loop and a second loop.

In a further embodiment, connecting a reinforcement construct to a first loop and a second loop includes looping the reinforcement construct about the first loop and passing the reinforcement construct through the second loop.

In a further embodiment, connecting a reinforcement construct to a first loop and a second loop includes passing the reinforcement construct through the first and second loops.

In a further embodiment, fixating a graft over top of a tissue defect with a knotless tensionable knotless fixation system includes tightening a first loop down to the graft to approximate the graft to the tissue defect, and tightening a second loop down to the graft to further approximate the graft to the tissue defect.

In a further embodiment, fixating a graft over top of a tissue defect with a knotless tensionable knotless fixation system includes securing a first tail portion of a reinforcement construct to a bone with a third knotless suture anchor, and securing a second tail portion of the reinforcement construct to the bone with a fourth knotless suture anchor.

In a further embodiment, a reinforcement construct of a knotless tensionable fixation system includes a double "V" pattern.

In a further embodiment, a reinforcement construct of a knotless tensionable fixation system includes a Z-shaped pattern.

In a further embodiment, a graft of a knotless tensionable fixation system is an osteochondral allograft and a tissue defect repaired by the graft is a cartilage defect.

In a further embodiment, a reinforcement construct of a knotless tensionable fixation system includes an absorbable suture.

In a further embodiment, a reinforcement construct of a knotless tensionable fixation system includes a nonabsorbable suture.

In a further embodiment, at least one knotless suture anchor of a knotless tensionable fixation system is a soft anchor assembly made exclusively of soft, suture-based materials.

An exemplary knotless tensionable fixation system for repairing a tissue defect may include, inter alia, a plurality of knotless suture anchors, an osteochondral allograft, and a reinforcement construct that is connectable to the plurality of knotless suture anchors and configured for fixating the osteochondral allograft over top of the tissue defect.

FIGS. 1-10 schematically illustrate various aspects associated with a surgical method for repairing a tissue defect 10 located within a joint 12. The joint 12 may include one or more bones 14. In an embodiment, the tissue defect 10 is a cartilage defect that includes localized areas of damaged articular cartilage and/or damaged subchondral portions of the bone 14 of the joint 12. In another embodiment, the tissue defect 10 is a soft tissue tear that requires reapproximation to the bone 14 in order to stabilize the joint 12. However, the surgical methods described in this disclosure could be utilized to repair any type of tissue defect.

The joint 12 may be any joint of the musculoskeletal system of the human body. For example, the surgical method described herein could be utilized to repair tissue defects associated with the knee, shoulder, hip, ankle, etc.

In an embodiment, the surgical method is performed as an arthroscopic procedure by working through various arthroscopic portals. However, the exemplary surgical method could alternatively be performed as an open procedure within the scope of this disclosure. As detailed below, the exemplary surgical method may be employed to deliver and fixate a graft 30 (see FIGS. 2-4) within the joint 12 for repairing the tissue defect 10 in a manner that enhances footprint compression to maximize graft-to-tissue contact.

Referring first to FIG. 1, after appropriately preparing the joint 12 (e.g., by debriding, creating a bleeding bone bed, preparing bone sockets, etc.), a first knotless suture anchor 16A and a second knotless suture anchor 16B may be implanted into the bone 14 at or near the tissue defect 10. Although two knotless suture anchors 16A, 16B are illustrated, a greater number of knotless suture anchors could be utilized as part of the surgical method. In an embodiment, the first knotless suture anchor 16A is placed at a superior pole 18 of the tissue defect 10, and the second knotless suture anchor 16B is placed at an inferior pole 20 of the tissue defect. However, other implantation locations could be selected based on the performing surgeon's own preferences.

A first suture loop 22 may be formed in the first knotless suture anchor 16A by splicing a suture 24 of the first knotless suture anchor 16A through itself. A second suture loop 26 may be similarly formed in the second knotless suture anchor 16B by splicing a suture 28 of the second knotless suture anchor 16B through itself. In an embodiment, the first suture loop 22 and the second suture loop 26 are each formed at a location that is outside of or external to the tissue defect 10.

The first and second knotless suture anchors 16A, 16B, including the first and second suture loops 22, 26, may be utilized to knotlessly fixate the graft 30 over the tissue defect 10. The surgical methods described herein are considered "knotless" because there is no need to tie any knots in the various structures for securing the graft 30 to the bone 14.

Figure 2:
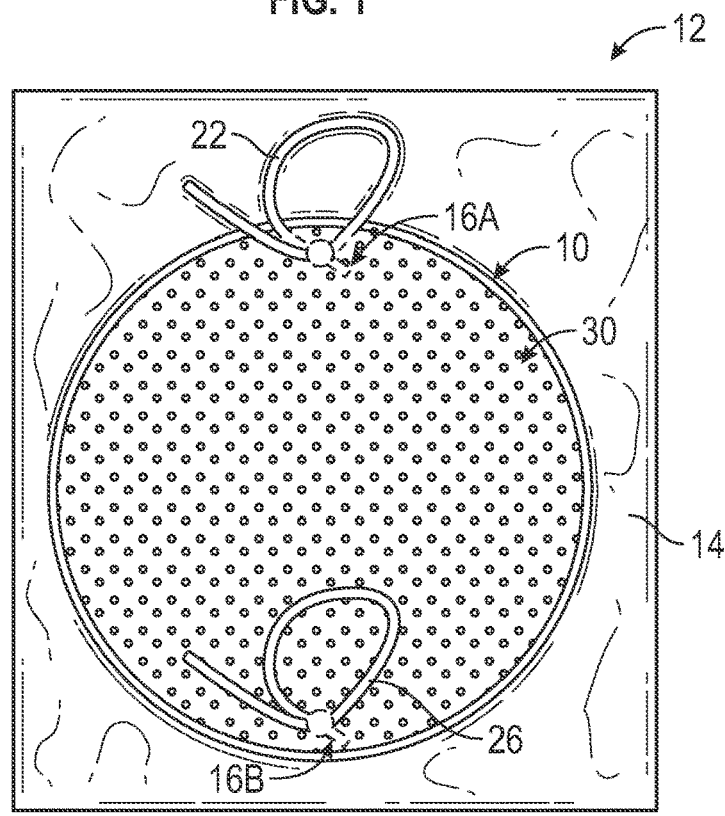
FIG. 2 illustrates another step of a surgical method for repairing a tissue defect.

Referring now to FIG. 2, the first and second suture loops 22, 26 may be passed through the graft 30, and the graft 30 may then be slid down over top of the tissue defect 10 in order to position the graft 30 at a desired fixation location within the joint 12. In an embodiment, the graft 30 may be positioned directly over top of the tissue defect 10. The graft 30 may serve as a scaffold over the tissue defect 10, thereby providing a tissue network that can potentially signal autologous cellular interactions for repairing the tissue defect 10.

Figure 3:
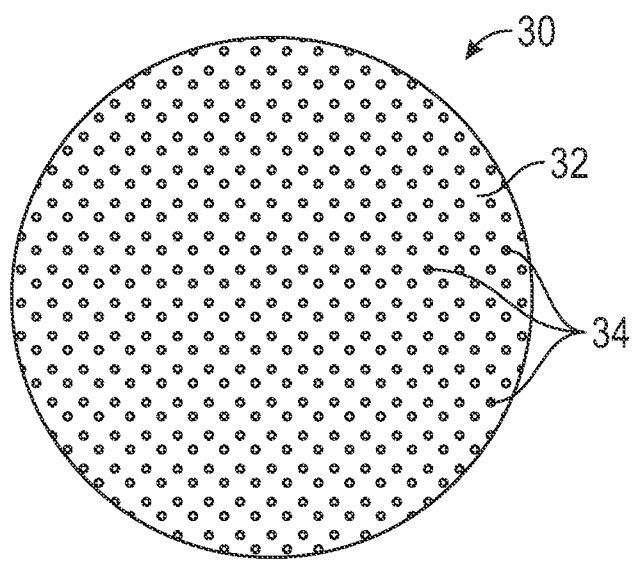
FIG. 3 illustrates an exemplary graft of a knotless tensionable fixation system.
Figure 4:
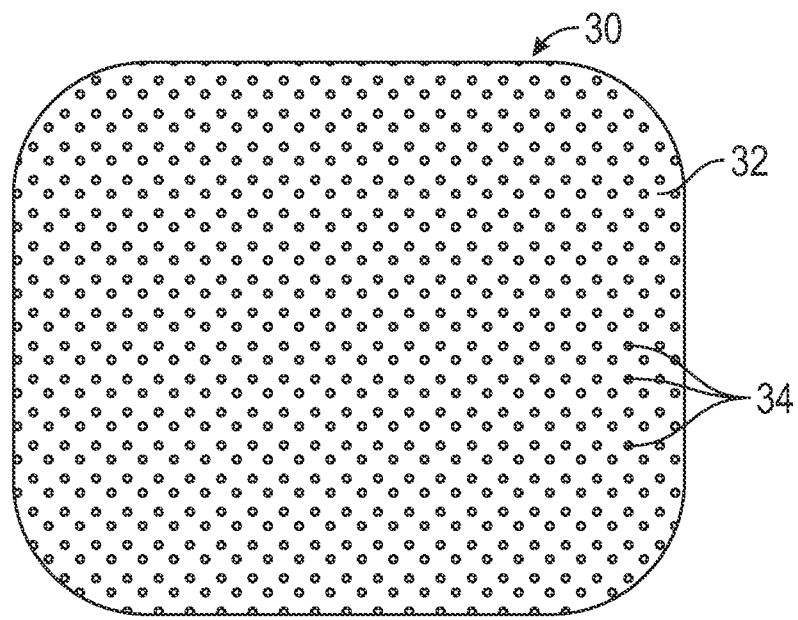
FIG. 4 illustrates another exemplary graft of a knotless tensionable fixation system.

An exemplary graft 30 is illustrated in FIG. 3. In an embodiment, the graft 30 includes a porous body 32 that includes a plurality of pores 34. The pores 34 may be configured to accommodate the first and second suture loops 22, 26, for example. Although shown as being porous, the graft 30 is not limited to such an embodiment. Moreover, the size and shape of the graft 30 are intended to be non-limiting.

In an embodiment, the porous body 32 is disk shaped (see FIG. 3). In another embodiment, the porous body 32 is rectangular shaped (see FIG. 4). However, the actual size and shape of the graft 30 utilized during the surgical method may vary and could be achieved by trimming the graft 30 down to a desired size and shape that matches that of the tissue defect 10.

In an embodiment, the graft 30 is an osteochondral allograft composed of viable chondrocytes, chondrogenic growth factors, and extracellular matrix proteins. In another embodiment, the graft 30 is a dermal allograft composed of an acellular dermal extracellular matrix. In another embodiment, the graft 30 is made of non-human tissue, such as synthetic materials, xeno materials, etc. In yet another embodiment, the graft 30 is an autograft. The exact material makeup of the graft 30 is not intended to limit this disclosure.

Figure 5:
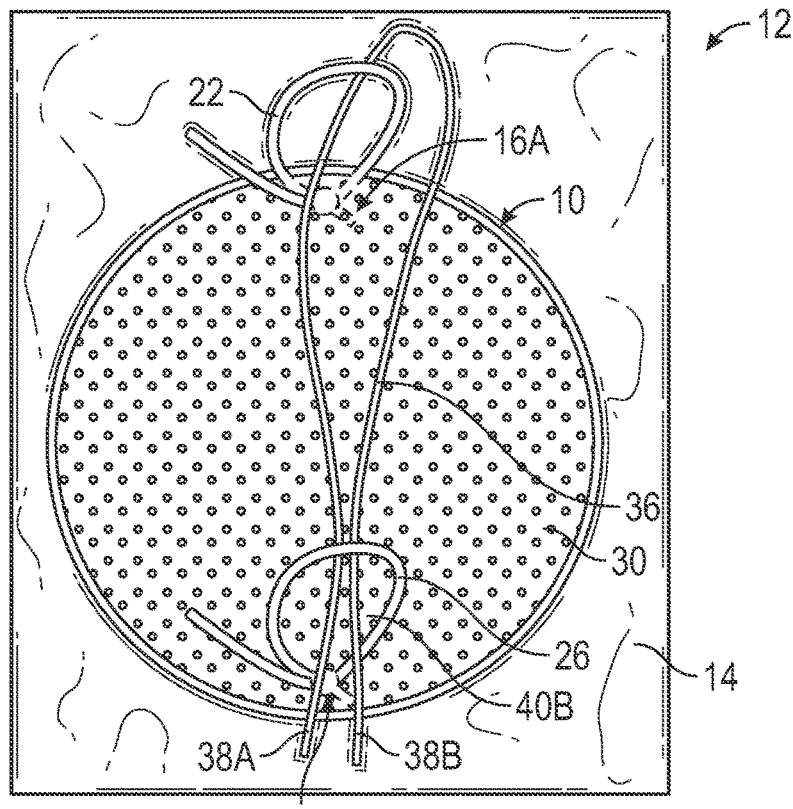
FIG. 5 illustrates another step of a surgical method for repairing a tissue defect.

Referring now to FIG. 5, the surgical method depicted in FIGS. 1 and 2 may continue by connecting a reinforcement construct 36 to the first and second suture loops 22, 26. Although one reinforcement construct 36 is shown, two or more reinforcement constructs 36 may be provided within the scope of this disclosure where greater footprint compression of the graft 30 is desired.

In an embodiment, the reinforcement construct 36 is connected to the first and second suture loops 22, 26 by looping the reinforcement construct 36 over a portion of the first suture loop 22 and passing first and second tail portions 38A, 38B of the reinforcement construct 36 through an opening 40B of the second suture loop 26 (see FIG. 5). In another embodiment, the reinforcement construct 36 is connected to the first and second loops 22, 26 by passing the first tail portion 38A through an opening 40A of the first suture loop 22 and passing the second tail portion 38B through the opening 40B of the second suture loop 26 (see FIG. 6). Other looping/passing configurations may be utilized for connecting the reinforcement construct 36 to the first and second suture loops 22, 26.

The reinforcement construct 36 may include a suture, multiple sutures, suture tape, or any other suture-like product. In an embodiment, the reinforcement construct 36 is an absorbable suture. In another embodiment, the reinforcement construct 36 is a nonabsorbable suture. In other embodiments, the first and second suture loops 22, 26 may also be absorbable.

Figure 7:
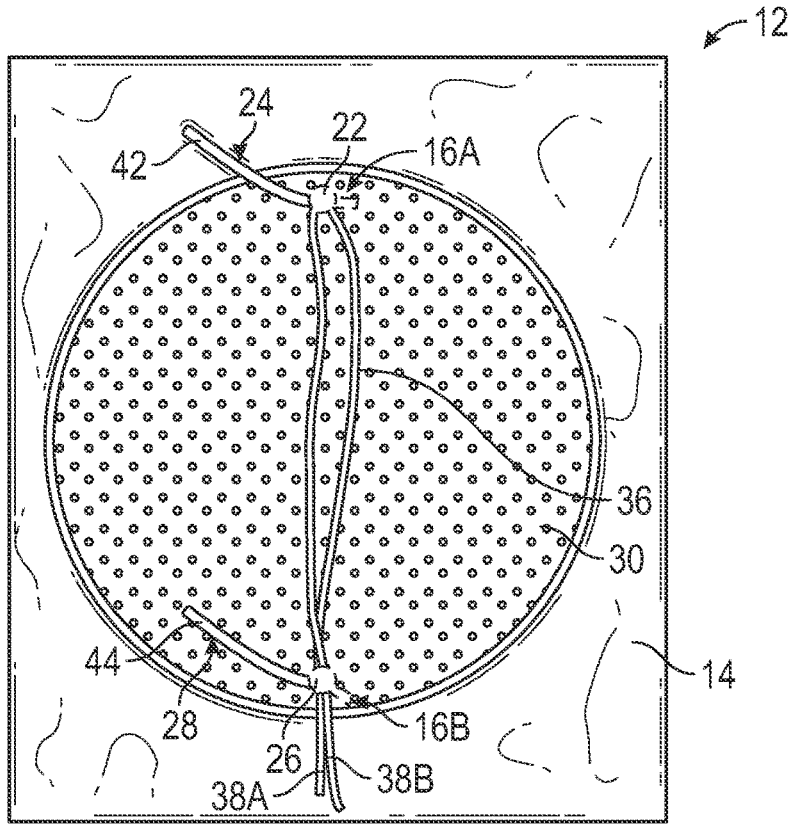
FIG. 7 illustrates another step of a surgical method for repairing a tissue defect.
Figure 8:
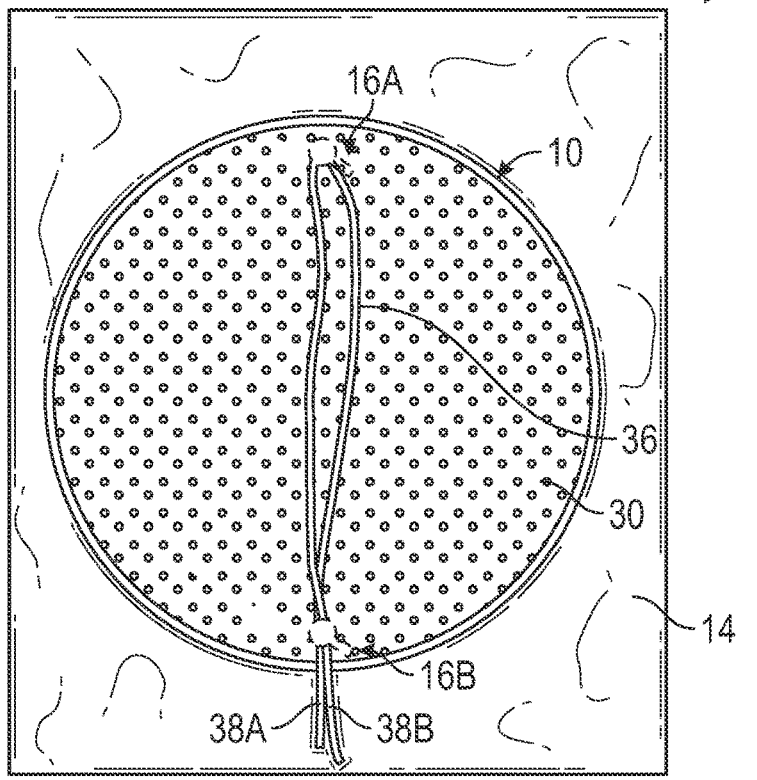
FIG. 8 illustrates another step of a surgical method for repairing a tissue defect.

As illustrated in FIG. 7, with the graft 30 pushed against the tissue defect 10/bone 14, the first and second suture loops 22, 26 may be tightened/constricted (e.g., reduced in size) while tensioning the first and second tail portions 38A, 38B. The first suture loop 22 may be constricted by pulling a suture tail 42 of the suture 24, and the second suture loop 26 may be constricted by pulling a suture tail 44 of the suture 28. The suture tail 42 and the suture tail 44 may then be removed (e.g., cut) from their respective suture loops 22, 26 (see FIG. 8).

Figure 18:
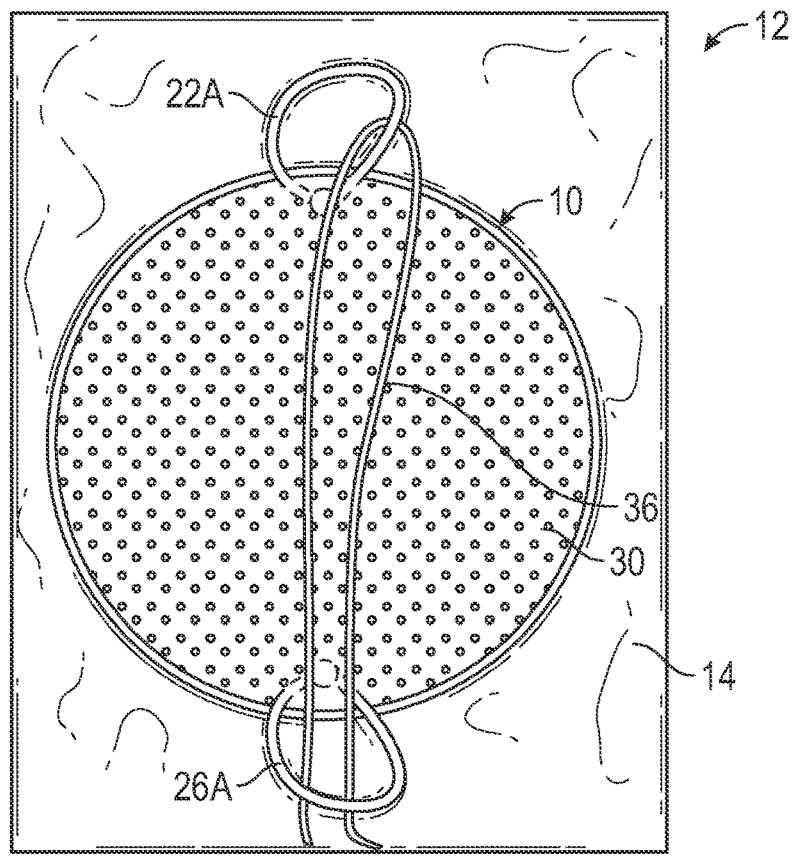
FIG. 18 illustrates the use of fixed suture loops as part of a surgical method for repairing a tissue defect.

The first and second suture loops 22, 26 of the system may therefore be adjustable loops. In other embodiments, first and second suture loops 22A, 26A of the system for performing the surgical method may be fixed, non-adjustable loops (see, e.g., FIG. 18). When the reinforcement construct 36 is tensioned, the first and second loops 22A, 26A may lay the loops 22A, 26A down against the graft 30.

Figure 9:
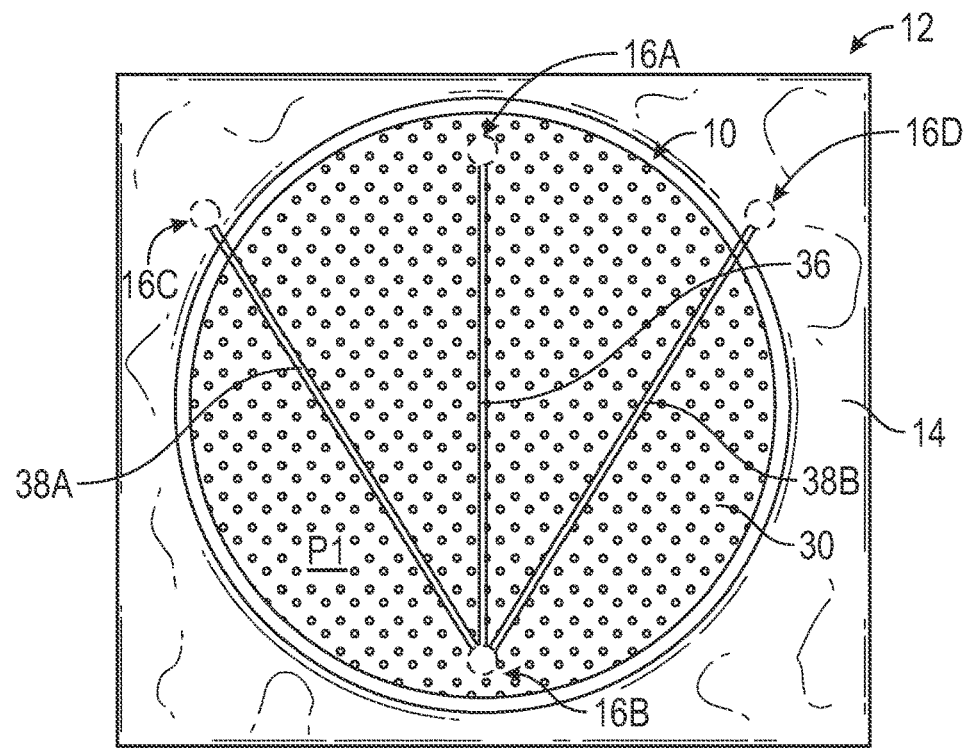
FIG. 9 illustrates a final repair construct of a surgical method for repairing the tissue defect.
Figure 10:
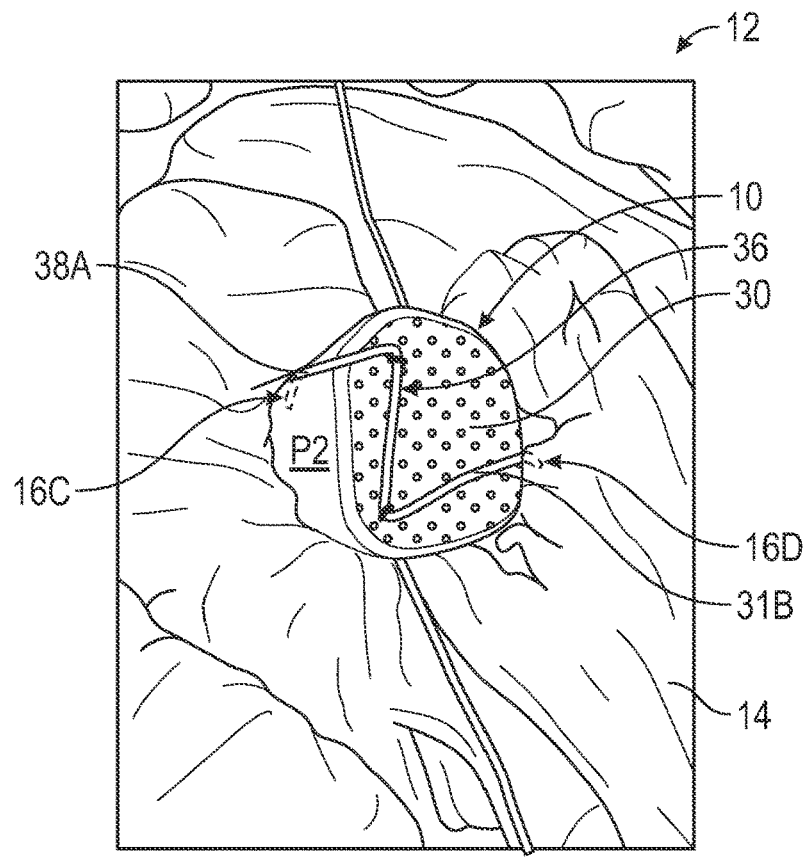
FIG. 10 illustrate an alternative final repair construct of a surgical method for repairing a tissue defect.

Next, as shown in FIGS. 9 and 10, the first and second tail portions 38A, 38B may be knotlessly fixated to the bone 14 to complete the repair. For example, the first tail portion 38A may be fixated to the bone 14 via a third knotless suture anchor 16C, and the second tail portion 38B may be fixated to the bone 14 via a fourth knotless suture anchor 16D. The first and second tail portions 38A, 38B may be fixated at locations of the bone 14 that are adjacent to the tissue defect 10. In an embodiment, the fixation location of the first tail portion 38A is located on an opposite side of the fixation location of the second tail portion 38B. Once the tail portions 38A, 38B are fixated, the reinforcement construct 36 may provide a fixed segment of material over the issue defect 10, thereby providing footprint compression that maximizes contact between the graft 30 and the underlying tissue.

When the reinforcement construct 36 is connected to the first and second suture loops 22, 26 in the manner depicted in FIG. 5 (e.g., by looping the reinforcement construct 36 over a portion of the first suture loop 22 and passing first and second tail portions 38A, 38B of the reinforcement construct 36 through the opening 40B of the second suture loop 26), the reinforcement construct 36 may exhibit a first fixation pattern P1 (see FIG. 9). In an embodiment, the first fixation pattern P1 is a double "V" pattern. The first fixation pattern P1 provides a multi-point fixation configuration for securing the graft 30.

Figure 6:
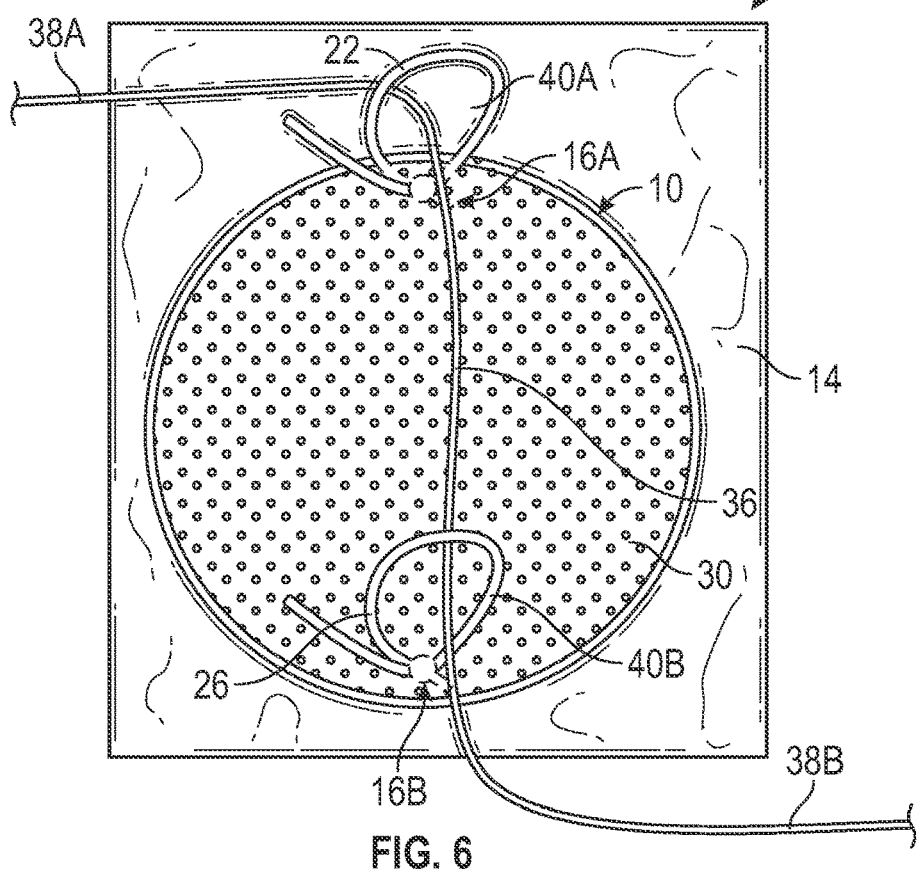
FIG. 6 illustrates an alternative routing configuration of a reinforcement construct of a knotless tensionable fixation system.

When the reinforcement construct 36 is connected to the first and second loops 22, 26 in the manner depicted in FIG. 6 (e.g., by passing the first tail portion 38A through the opening 40A of the first suture loop 22 and passing the second tail portion 38B through the opening 40B of the second suture loop 26), the reinforcement construct 36 may exhibit a second fixation pattern P2 (see FIG. 10). In an embodiment, the second fixation pattern P2 is a Z-shaped pattern. The second fixation pattern P2 provides a multi-point fixation configuration for securing the graft 30. Other fixation patterns may be achieved by modifying the fixation locations of the first and second tail portions 38A, 38B and/or by using additional knotless suture anchors and/or reinforcement constructs 36 as part of the surgical method.

FIGS. 11-16 illustrate exemplary knotless suture anchors that can be utilized as part of a knotless tensionable fixation system for performing the surgical method steps described above. Knotless suture anchors similar to those shown in FIGS. 11-16 may be utilized either alone or in combination with one another to fixate the graft 30 to the bone 14 during the surgical method.

Figure 11:
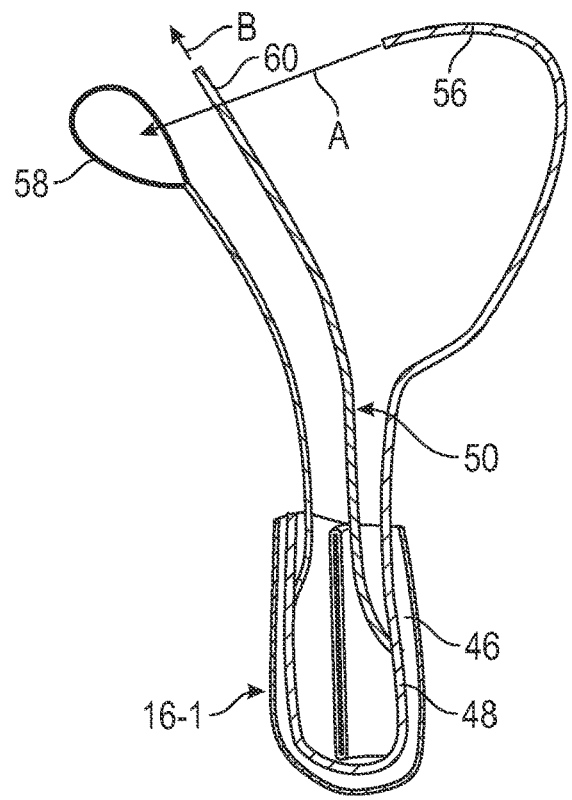
FIGS. 11 and 12 illustrate an exemplary knotless suture anchor.
Figure 12:
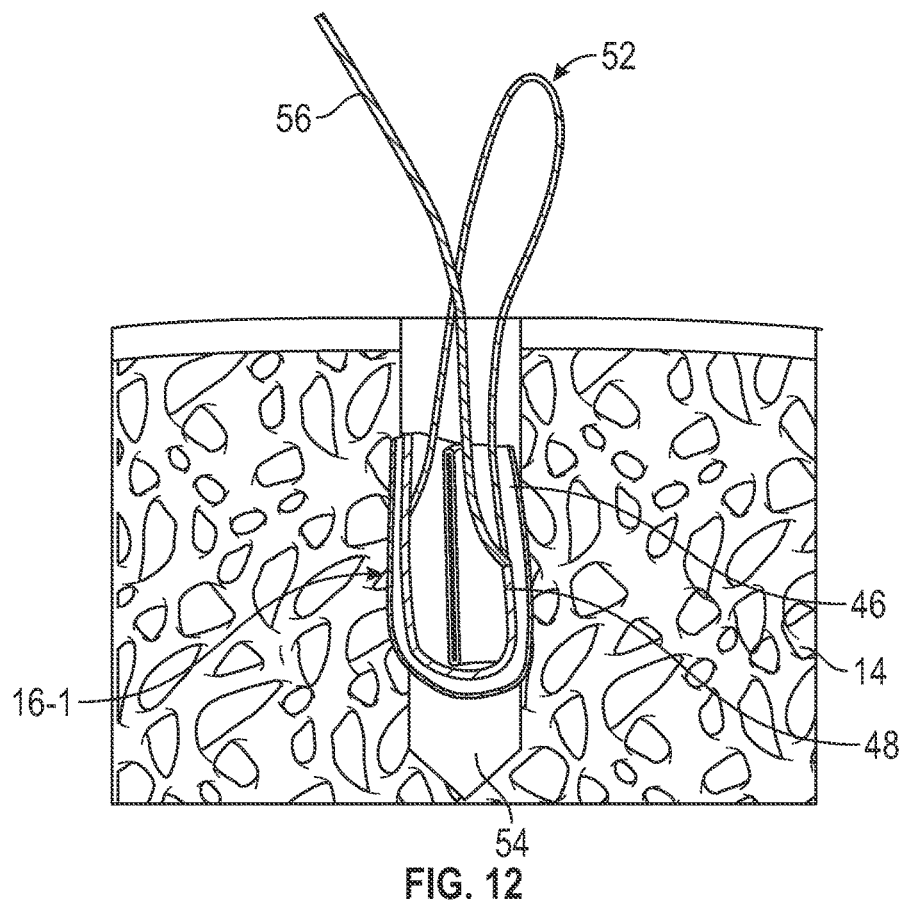

An exemplary knotless suture anchor 16-1 is illustrated in FIGS. 11 and 12. In this embodiment, the knotless suture anchor 16-1 is a "soft" anchor assembly made exclusively of soft, suture-based materials. The suture-based materials may include soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. The soft, suture-based materials confer the knotless suture anchor 16-1 with the ability to be inserted into bone sockets/holes and bunch together, collapse, expand and/or change shape to fixate within the socket/hole.

The knotless suture anchor 16-1 may include an anchor body 46 and a flexible suture strand 48 received through the anchor body 46. A shuttle device 50 may be spliced through portions of the flexible suture strand 48. The shuttle device 50 may be a passing wire or another suture, for example.

The anchor body 46 of the knotless suture anchor 16-1 may be inserted into a socket 54 formed in the bone 14 (see FIG. 12). The socket 54 may be a preformed opening formed in the bone 14 that is configured for receiving the anchor body 46.

The shuttle device 50 may be pre-assembled to the flexible suture strand 48 as shown in FIG. 11, and the flexible suture strand 48 may form a suture loop 52 (e.g., the equivalent of the suture loops 22, 26 of FIG. 1) after the flexible suture strand 48 is shuttled through itself as shown in FIG. 12. For example, a suture tail 56 of the flexible suture strand 48 may be passed through an eyelet 58 of the shuttle device 50 (in the direction of arrow A of FIG. 11), and then a free end 60 of the shuttle device 50 may be pulled (in the direction of arrow B of FIG. 11) to allow flexible suture strand 48 to pass through itself and form the suture loop 52. The perimeter of suture loop 52 is adjustable to allow the construct to be self-cinching and to adjust the tension on the graft to be fixated.

In an exemplary embodiment, the knotless suture anchors 16A, 16B of the knotless tensionable fixation system may include the design of the knotless suture anchor 16-1 for performing the surgical method steps discussed above.

Figure 13:
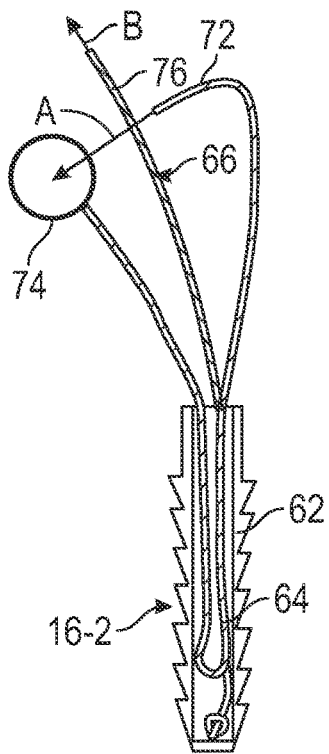
FIGS. 13 and 14 illustrate another exemplary knotless suture anchor.
Figure 14:
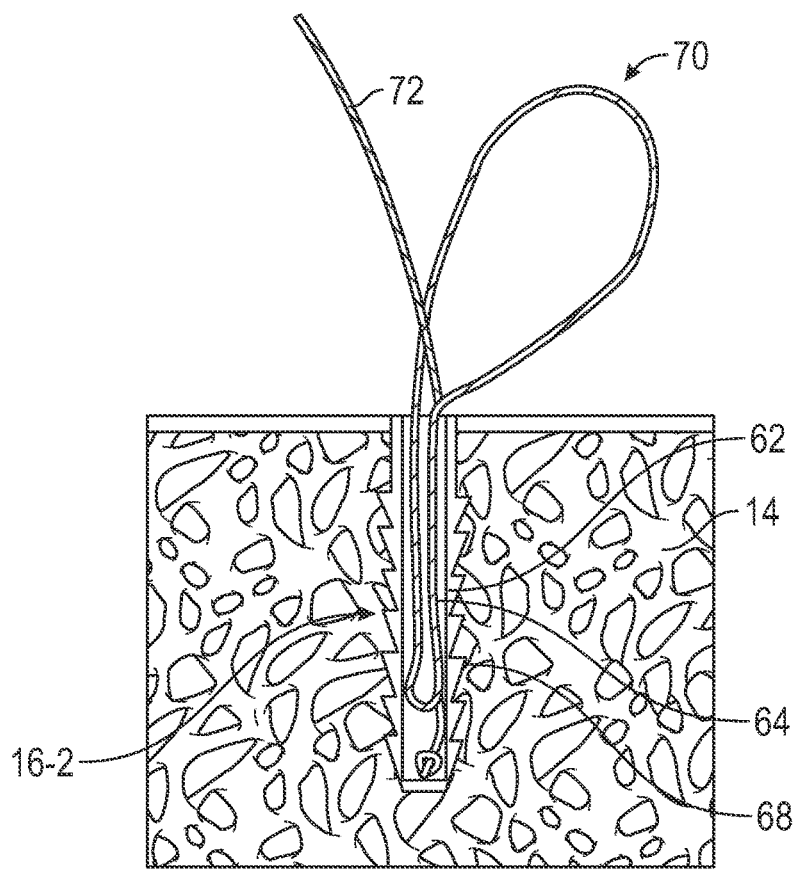

Another exemplary knotless suture anchor 16-2 is illustrated in FIGS. 13 and 14. The knotless suture anchor 16-2 may include an anchor body 62 and a flexible suture strand 64 received through the anchor body 62. In this embodiment, the anchor body 62 is a relatively rigid plastic body and thus the knotless suture anchor 16-2 is not considered to be a "soft" anchor assembly.

A shuttle device 66 may be spliced through portions of the flexible suture strand 64. The shuttle device 66 may be a passing wire or another suture, for example.

The anchor body 62 of the knotless suture anchor 16-2 may be inserted into a socket 68 formed in the bone 14 (see FIG. 14). The socket 68 may be a preformed opening formed in the bone 14 that is configured for receiving the anchor body 62.

The shuttle device 66 may be pre-assembled to the flexible suture strand 64 as shown in FIG. 13 and may be utilized to may form a suture loop 70 (e.g., the equivalent of the suture loops 22, 26 of FIG. 1) after the flexible suture strand 64 is shuttled through itself as shown in FIG. 14. For example, a suture tail 72 of the flexible suture strand 64 may be passed through an eyelet 74 of the shuttle device 66 (in the direction of arrow A of FIG. 13), and then a free end 76 of the shuttle device 66 may be pulled (in the direction of arrow B of FIG. 13) to allow the flexible suture strand 64 to pass through itself and form the suture loop 70. The perimeter of suture loop 70 is adjustable to allow the construct to be self-cinching and to adjust the tension on the graft to be fixated.

In an exemplary embodiment, the knotless suture anchors 16A, 16B of the knotless tensionable fixation system may include the design of the knotless suture anchor 16-2 (rather than that of the knotless suture anchor 16-1, for example) for performing the surgical method steps discussed above.

Figure 15:
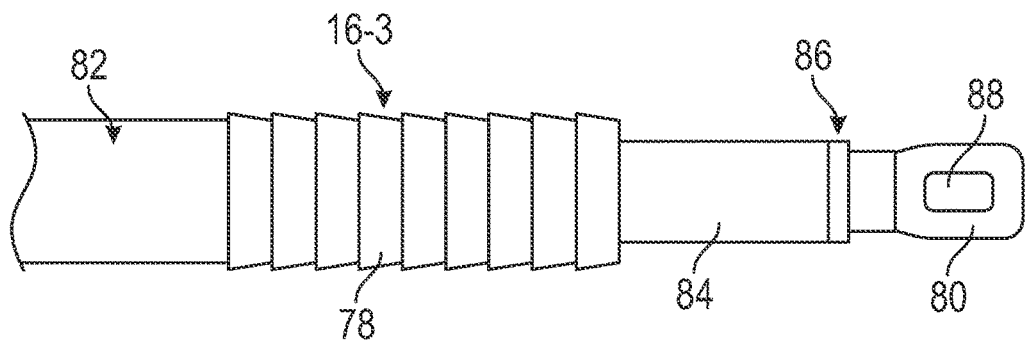
FIGS. 15 and 16 illustrate yet another exemplary knotless suture anchor.
Figure 16:
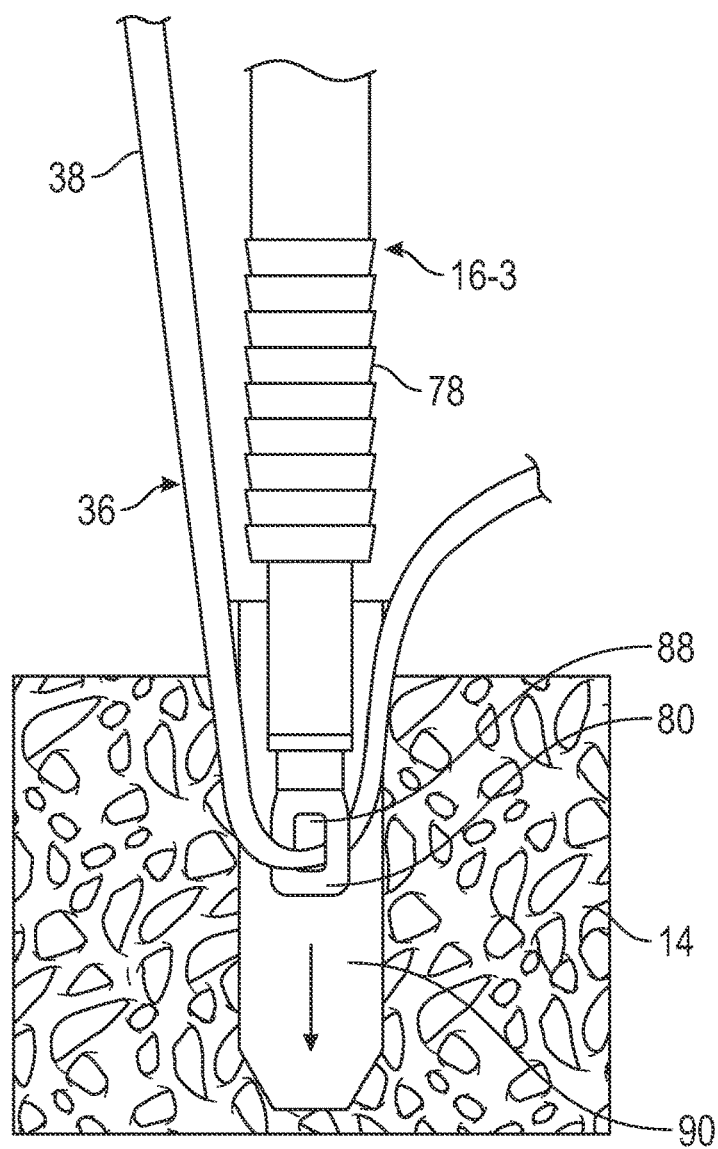

Yet another exemplary knotless suture anchor 16-3 is illustrated in FIGS. 15 and 16. The knotless suture anchor 16-3 may include an anchor body 78 and an eyelet 80. In this embodiment, the anchor body 78 and the eyelet 80 are relatively rigid plastic structures and thus the knotless suture anchor 16-3 is not considered to be a "soft" anchor assembly.

The anchor body 78 may be pre-loaded onto a driver 82. The anchor body 78 may be configured as a screw or an interference plug that is appropriately cannulated for receiving a shaft 84 of the driver 82. The eyelet 80 may be provided at a distal end 86 of the driver 82. The eyelet 80 may be releasably attached to the distal end 86. The eyelet 80 may include an aperture 88 for receiving one or more flexible strands (e.g., one or more tail portions 38 of the reinforcement construct 36).

The anchor body 78 and the eyelet 80 of the knotless suture anchor 16-3 may be inserted into a socket 90 formed in the bone 14 (see FIG. 16). The socket 90 may be a preformed opening formed in the bone 14 that is configured for receiving the anchor body 78 and the eyelet 80. One of the tail portions 38 of the reinforcement construct 36 may be loaded through the eyelet 80, and then the eyelet 80 may be inserted into the socket 90. The tail portion 38 may then be tensioned prior to moving the anchor body 78 down toward the eyelet 80 within the socket 90. Once implanted within the socket 90, the anchor body 78 may trap the reinforcement construct 36 between the bone 14 and the anchor body 78 in order to fixate the reinforcement construct 36 in place.

In an exemplary embodiment, the knotless suture anchors 16C, 16D of the knotless tensionable fixation system may include the design of the knotless suture anchor 16-3 for performing the surgical method discussed above. However, any combination of knotless suture anchors may be utilized to knotlessly fixate the graft 30 during the surgical method.

Figure 17:
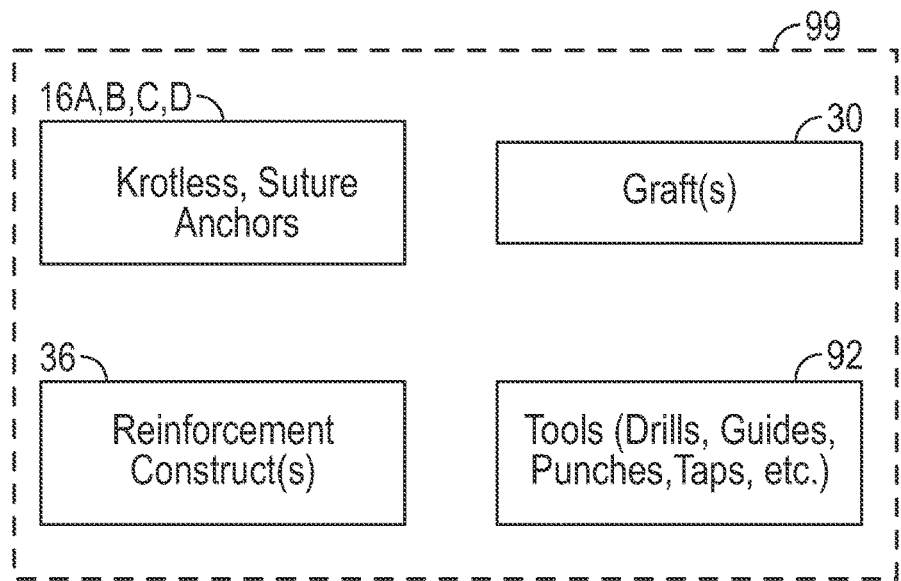
FIG. 17 schematically illustrates an exemplary knotless tensionable fixation system.

FIG. 17 schematically illustrates an exemplary knotless tensionable fixation system 99 that may be provided for performing the surgical method steps discussed above. The knotless tensionable fixation system 99 may be provided in the form of a surgical kit that includes all the necessary tools and components for performing surgical methods for repairing tissue defects. In an embodiment, the knotless tensionable fixation system 99 may include at least the following components:

1. At least (4) knotless suture anchors 16A, 16B, 16C, 16D;
2. One or more grafts 30;
3. One or more reinforcement constructs 36; and
4. Tools 92 (e.g., disposable drills, drill guides, punches, taps, etc.) for inserting the knotless suture anchors.

Other components or different combinations of components could be provided as part of the knotless tensionable fixation system 99 within the scope of this disclosure. For example, the knotless tensionable fixation system 99 could include various templates, scorers, curettes, and/or measuring devices that may be utilized to help prepare the tissue defect for perform the surgical method discussed herein.

The knotless tensionable fixation systems described herein may be utilized to perform surgical methods for repairing tissue defects. The proposed systems provide a multi-point fixation configuration for fixating a graft over the tissue defect. A reinforcement construct of the system provides a fixed segment of material over top of the graft, thereby maximizing graft-to-tissue contact.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method for repairing a tissue defect, comprising:
   inserting a first knotless suture anchor into a bone;
   creating a first loop in the first knotless suture anchor;
   inserting a second knotless suture anchor into the bone;
   creating a second loop in the second knotless suture anchor;
   passing the first loop and the second loop through a graft;
   passing a reinforcement construct through the first loop or looping the reinforcement construct about the first loop;
   passing the reinforcement construct through the second loop or looping the reinforcement construct about the second loop;
   tightening the first loop down to the graft to approximate the graft to the tissue defect;
   tightening the second loop down to the graft to further approximate the graft to the tissue defect,
   securing a first tail portion of the reinforcement construct to the bone with a third knotless suture anchor; and
   securing a second tail portion of the reinforcement construct to the bone with a fourth knotless suture anchor, and
   wherein the first tail portion and the second tail portion are secured to the bone on opposite lateral sides of the graft and are each located beyond a respective lateral edge of the graft,
   wherein the reinforcement construct extends over top of the graft to compresses the graft to the tissue defect after the securing.

2. The surgical method as recited in claim 1, wherein the graft is an osteochondral allograft.

3. The surgical method as recited in claim 1, wherein the graft is a dermal allograft.

4. The surgical method as recited in claim 1, wherein the reinforcement construct is an absorbable suture.

5. The surgical method as recited in claim 1, wherein the reinforcement construct is a nonabsorbable suture.

6. A surgical method for repairing a tissue defect, comprising:
   fixating a graft over top of a tissue defect with a knotless tensionable fixation system,
   wherein the knotless tensionable fixation system includes a plurality of knotless suture anchors, the graft, and a reinforcement construct,
   wherein the reinforcement construct establishes a fixed segment of material over the graft and is secured in place by the plurality of knotless suture anchors, and
   wherein at least two knotless suture anchors of the plurality of knotless suture anchors are located beneath the graft after fixating the graft over top of the tissue defect,
   wherein at least two other knotless suture anchors of the plurality of knotless suture anchors are located on opposite sides of the graft and not underneath the graft after fixating the graft over top of the tissue defect.

7. The surgical method as recited in claim 6, wherein the fixating includes:
   inserting a first knotless suture anchor of the plurality of knotless suture anchors into a bone;
   creating a first loop in the first knotless suture anchor;
   inserting a second knotless suture anchor of the plurality of knotless suture anchors into the bone; and
   creating a second loop in the second knotless suture anchor.

8. The surgical method as recited in claim 7, wherein the fixating includes:
   passing the first loop and the second loop through the graft.

9. The surgical method as recited in claim 8, wherein the fixating includes:
   connecting the reinforcement construct to the first loop and the second loop.

10. The surgical method as recited in claim 9, wherein the connecting includes:
    looping the reinforcement construct about the first loop; and
    passing the reinforcement construct through the second loop.

11. The surgical method as recited in claim 9, wherein the connecting includes:
    passing the reinforcement construct through the first loop and the second loop.

12. The surgical method as recited in claim 9, wherein the fixating includes:
    tightening the first loop down to the graft to approximate the graft to the tissue defect; and
    tightening the second loop down to the graft to further approximate the graft to the tissue defect.

13. The surgical method as recited in claim 12, wherein the fixating includes:
    securing a first tail portion of the reinforcement construct to the bone with a third knotless suture anchor of the plurality of knotless suture anchors; and
    securing a second tail portion of the reinforcement construct to the bone with a fourth knotless suture anchor of the plurality of knotless suture anchors.

14. The surgical method as recited in claim 13, wherein the reinforcement construct includes a double "V" pattern after securing the first and second tail portions.

15. The surgical method as recited in claim 13, wherein the reinforcement construct includes a Z-shaped pattern after securing the first and second tail portions.

16. The surgical method as recited in claim 6, wherein the graft is an osteochondral allograft and the tissue defect is a cartilage defect.

17. The surgical method as recited in claim 6, wherein the reinforcement construct is an absorbable suture.

18. The surgical method as recited in claim 6, wherein the reinforcement construct is a nonabsorbable suture.

19. The surgical method as recited in claim 6, wherein at least one of the plurality of knotless suture anchors is a soft anchor assembly made exclusively of soft, suture-based materials.

20. A surgical method for repairing a tissue defect, comprising:
 inserting a first knotless suture anchor into a bone;
 creating a first loop in the first knotless suture anchor, wherein creating the first loop includes splicing a first suture of the first knotless suture anchor through itself;
 inserting a second knotless suture anchor into the bone;
 creating a second loop in the second knotless suture anchor, wherein creating the second loop includes splicing a second suture of the second knotless suture anchor through itself;
 passing the first loop and the second loop through a graft;
 passing a reinforcement construct through the first loop or looping the reinforcement construct about the first loop;
 passing the reinforcement construct through the second loop or looping the reinforcement construct about the second loop;
 tightening the first loop down to the graft to approximate the graft to the tissue defect;
 tightening the second loop down to the graft to further approximate the graft to the tissue defect,
 securing a first tail portion of the reinforcement construct to the bone with a third knotless suture anchor;
 securing a second tail portion of the reinforcement construct to the bone with a fourth knotless suture anchor, and
 wherein the reinforcement construct extends over top of the graft to compresses the graft to the tissue defect after the securing,
 wherein, after the tightening, the first knotless suture anchor and the second knotless suture anchor are located beneath the graft,
 wherein, after the securing, the third knotless suture anchor and the fourth knotless suture anchor are located on opposite sides of the graft and are laterally beyond an edge of the graft.

* * * * *